United States Patent [19]

Matsunaga et al.

[11] Patent Number: 5,079,383

[45] Date of Patent: Jan. 7, 1992

[54] METHOD OF CONDENSING N-PHENYL CARBAMATES

[75] Inventors: Fujihisa Matsunaga, Wakayama; Mitsuki Yasuhara, Chiba, both of Japan

[73] Assignee: Mitsui Petrochemical Industries, Ltd., Tokyo, Japan

[21] Appl. No.: 556,993

[22] Filed: Jul. 25, 1990

[30] Foreign Application Priority Data

Jul. 27, 1989 [JP] Japan .................. 1-195328

[51] Int. Cl.$^5$ .................. C07C 269/00; C07C 271/00
[52] U.S. Cl. ........................ 560/25; 560/27; 560/30; 560/31; 560/32; 560/33
[58] Field of Search ............. 560/25, 27, 30, 31, 560/32, 33

[56] References Cited

U.S. PATENT DOCUMENTS 2,946,768  7/1960  Klauke et al. .................. 260/65
4,699,994  1/1987  Ikariya et al. .................. 560/25

*Primary Examiner*—Jose G. Dees
*Assistant Examiner*—Porfirio Nazario
*Attorney, Agent, or Firm*—Birch, Stewart, Kolasch & Birch

[57] ABSTRACT

A process for producing 4,4'-diphenylmethane dicarbamates through one-stage condensation by reacting N-phenyl carbamates with a methylenating agent in presence of a zinc halide, as a catalyst. 4,4'-diphenylmethane dicarbamates can be produced with high selectivity and in high yield.

8 Claims, No Drawings

METHOD OF CONDENSING N-PHENYL CARBAMATES

BACKGROUND OF THE INVENTION

The present invention relates to a process by which binuclear 4,4-di-phenylmethane dicarbamates serving as precursors of 4,4'-diphenylmethane diisocyanate (4,4'-MDI or commonly referred to as "pure MDI") can be produced with high selectivity and in high yield by reacting N-phenyl carbamates with a methylenating agent. The demand at the present time for 4,4'-diphenylmethane diisocyanate (pure MDI) has rapidly increased since it can be used as a starting material for various products including adhesives, paints, spundex fibers and urethane elastomers. Under these circumstances, a great benefit would result from providing a process in which 4,4'-diphenylmethane dicarbamates serving as starting materials for pure MDI can be produced in an industrially advantageous way.

A conventional known process for producing diphenylmethane dicarbamates comprises reacting N-phenyl carbamates with methylenating agents such as trioxane, formalin (aqueous solution of formaldehyde), dimethoxymethane, paraformaldehyde and diacetoxymethane in the presence of acid catalysts such as organic sulfonic acids, polysulfuric acid, mineral acids, Lewis acids on graphite, sulfonate based cation exchangers, heteropolyphosphoric acid, clay minerals, and metal phosphates.

Various versions of this process have been proposed and in one example, the reaction is carried out in the presence of organic solvents such as nitrobenzene, benzene and sulfolane using as acid catalysts, a variety of Bronsted and Lewis acids including trifluoromethanesulfonic acid, 96% sulfuric acid, fluorinated sulfonic or carboxylic acid resins, solid sulfuric acid, iron chloride on graphite, boron trifluoride and 40% ferric chloride (see Unexamined Published Japanese Patent Application Nos. 57550/1980, 115862/1980, 129260/1980, 160012/1980, 171952/1982, 171953/1982, 171954/1982 and 62151/1983). However, due to the high acidic strength of the catalysts used, the yield of the 4,4'-diphenylmethane dicarbamates produced is as low as 30-50% and tri- and more nuclear polymethylenepolyphenyl carbamates, namely, polynuclear compounds represented by the general formula:

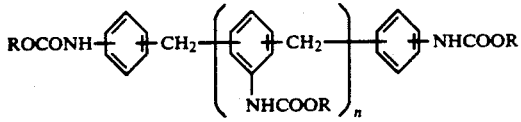

(R: alkyl, aralkyl or phenyl group) are formed as by-products in large quantities. Hence, this approach is not satisfactory for producing suitable starting materials for pure MDI.

With a view to solving this problem, it has been proposed to use aqueous acid solutions having concentrations of 10 wt% and higher (Unexamined Published Japanese Paten& Application Nos. 81850/1980 and 81851/1980) or trifluoromethanesulfonic acid in aqueous solvents (Unexamined Published Japanese Patent Application No. 79358/1980). In these methods, the strength of acid catalysts is sufficiently reduced by the presence of water to bring about a preferred result in that the formation of the tri- and more nuclear polymethylenepolyphenyl carbamates as by-products is suppressed. On the other hand, the reaction rate decreases to cause difficulty in completing the reaction and compounds having a methyleneamino bond (—$CH_2$—N—) that are precursors of 4,4'-diphenylmethane dicarbamates, namely, intermediates represented by the general formula:

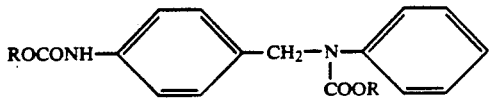

(R: alkyl, aralkyl or phenyl group) remain in large quantities in the reaction solution.

It is difficult to separate the compounds having a methyleneamino bond from 4,4'-diphenylmethane dicarbamates If the mixture of these compounds is decomposed thermally, diphenylmethane diisocyanate would be generated from 4,4'-diphenylmethane dicarbamates but no isocyanate would form from the compounds having a methyleneamino bond. These compounds do not merely remain unreacted and it has been pointed out that these compounds would cause various side reactions with isocyanate to substantially lower the yield of the desired isocyanate (Unexamined Published Japanese Patent application No. 106453/1984).

In order to insure that no compounds having a methyleneamino bond would remain unreacted in the reaction solution, it has been proposed that after condensing N-phenyl carbamates with a methylenating agent in the presence of an aqueous solution of an inorganic acid as a catalyst, the catalyst should be separated and the organic reaction mixture be subjected to further reaction in the presence of a carboxylic acid ($pKa \leq 4$) catalyst so that the compounds having a methyleneamino bond are isomerized to 4,4'-diphenylmethane dicarbamates (Unexamined Published Japanese Patent Application No. 106453/1984).

This method not only achieves the intended object (i.e., producing a reaction solution that does not contain any intermediate compounds having a methyleneamino bond) but also suppresses the formation of the by-product, polymethylenepolyphenyl carbamate. Nevertheless, the reaction would unavoidably proceed in two stages of condensation and isomerization and this greatly adds to the complexity of the production process. Further, carboxylic acids of $pKa \leq 4$ typified by strong acids such as trifluoroacetic acid are used as isomerization catalysts, so in order to protect against the corrosive action of such acids, the reactor must be made of an expensive material and this would increase the cost of producing the desired pure MID.

SUMMARY OF THE INVENTION

The present invention has been accomplished in order to overcome the aforementioned difficulties of the prior art and its principal object is to provide an industrially advantageous method of condensing N-phenyl carbamates by which binuclear 4,4'-diphenylmethane dicarbmates can be produced with high selectivity and in high yield by a simple procedure of one-stage reaction (condensation) with minimum occurrence of by-products such as tri- and more nuclear polymethylenepolyphenyl carbamates and intermediate compounds having a methyleneamino bond.

As a result of the intensive studies conducted on various methods for condensing N-phenyl carbamates, the present inventors found unexpectedly that zinc halides not only has high catalytic activity but also exhibits excellent performance in producing 4,4'-diphenylmethane dicarbamates with high selectivity and in high yield without generating by-products such as tri- and more nuclear polymethylenepolyphenyl carbamates and intermediate compounds having a methyleneamino bond.

Basically, the present invention provides a process for producing diphenylmethane dicarbamates through one-stage condensation by reacting N-phenyl carbamates with a methylenating agent. In accordance with the present invention, 4,4'-diphenylmethane dicarbamates can be produced with high selectivity and in high yield by using a very weak acidic zinc halide as a catalyst, preferably in the presence of an organic solvent. Zinc chloride ($ZnCl_2$) or zinc bromide ($ZnBr_2$) is preferably used as a zinc halide.

The primary object of the present invention is to provide a process by which 4,4'-diphenylmethane dicarbamates suitable for producing pure MDI by a thermal decomposition reaction can be produced from N-phenyl carbamates and a methylenating agent on an industrial scale at low cost.

DETAILED DESCRIPTION OF THE INVENTION

The N-phenyl carbamates used as a starting material in the method of the present invention are compounds represented by the following general formula:

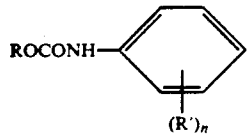

where R is a $C_1$–$C_4$ substituted or unsubstituted alkyl, a $C_5$–$C_9$ cycloalkyl, or an aralkyl, a phenyl group having at least a $C_1$–$C_4$ straight-chain or branched alkyl group on its benzene ring; R' is a substituent such as hydrogen atom, a $C_1$–$C_4$ alkyl group, a halogen atom, nitro group, cyano group, a $C_1$–$C_4$ alkoxy group, and an aralkyl or phenyl group having at least a $C_1$–$C_4$ straight-chain or branched alkyl group on its benzene ring, provided that R' is bonded to the urethane group in the ortho- or meta-position; and n is an integer of 0–4, provided that when $n \geq 2$, R' may assume the same or different substituents.

Examples of the N-phenyl carbamates having the general formula set forth above include: methyl N-phenylcarbamate, ethyl N-phenylcarbamate, n-propyl N-phenylcarbamate, iso-propyl N-phenylcarbamate, n-butyl N-phenylcarbamate, iso-butyl N-phenylcarbamate, tert-butyl N-phenylcarbamate, pentyl N-phenylcarbamate, hexyl N-phenylcarbamate, cyclohexyl N-phenylcarbamate, methyl N-o- or m-tolylcarbamate, ethyl N-o-or m-tolylcarbamate, propyl N-o- or m-tolyl carbamate (or isomers thereof), butyl N-o- or m-tolylcarbamate (or isomers thereof), methyl N-o- or m-chlorophenylcarbamate, ethyl N-o-or m-chlorophenylcarbamate, propyl N-o- or m-chlorophenylcarbamate (or isomers thereof), butyl N-o or m-chlorophenylcarbamate (or isomers thereof), methyl N-2,6-dimethylphenylcarbamate, ethyl N-2,6-dimethylphenylcarbamate, propyl N-2,6-dimethylphenylcarbamate (or isomers thereof) and butyl N-2,6-dimethylphenylcarbamate (or isomers thereof).

Preferred N-phenyl carbamates are methyl N-phenylcarbamate, ethyl N-phenylcarbamate and propyl N-phenylcarbamate, and methyl N-phenylcarbamate is more preferred.

Examples of the methylenating agent that can be used in the present invention include formalin (aqueous solution of formaldehyde), paraformaldehyde, trioxane, tetraoxane, lower alkoxymethanes such as dimethoxymethane, diethoxymethane and dipropoxymethane, and diacyloxymethanes having a lower carboxy group such as diacetoxymethane and dipropyloxymethane. These alkylating agents may be used either on their own or as admixtures. Formalin and paraformaldehyde are preferably used as alkylating agents. A particularly preferred alkylating agent is formalin and one of the features of the present invention is that 4,4'-diphenylmethane dicarbamates can be produced with high selectivity and in high yield using formalin that is available as the least expensive alkylating agent.

A zinc halide is used as a catalyst in the present invention and zinc chloride ($ZnCl_2$) and zinc bromide ($ZnBr_2$) are preferred examples. These catalysts may be used either on their own or as admixtures. The manner in which these catalysts are used is in no way limited to any physical form and they may be in powder form, in liquid state or may be supported on carriers.

The method of the present invention may be implemented in the absence of solvents but, more preferably, organic solvents are used. Organic solvents that can be used in the present invention include aliphatic or aromatic compounds having an electron-attracting substituent, as well as aromatic compounds having a halogen atom. A particularly preferred electrophilic substituent is a nitro group. Specific examples of organic solvents that contain a nitro group as an electron-attracting substituent include: $C_1$–$C_4$ lower aliphatic nitro compounds such as nitromethane, nitroethane, nitropropane (or isomers thereof) and nitrobutane (or isomers thereof), unsubstituted aromatic nitro compounds such as nitrobezene and dinitrobenzene, and $C_1$–$C_4$ lower alkyl substituted aromatic nitro compounds such as nitrotoluene (or isomers thereof), dinitrotoluene, nitroethylbenzene, dinitroethylbenzene, nitropropylbenzene (or isomers thereof), dinitropropylbenzene (or isomers thereof), nitrobutyl toluene (or isomers thereof) and dinitrobutyl toluene (or isomers thereof). Exemplary aromatic halogen compounds include chlorobenzene, bromobenzene, iodobenzene, dichlorobenzene, dibromobenzene, diiodobenzene, chlorobromobenzene, etc. These solvents may be used either on their own or as admixtures. Preferred organic solvents are nitrobenzene, nitromethane and chlorobenzene, with nitrobenzene being particularly preferred.

In the practice of the method of the present invention, the molar ratio of N-phenyl carbamates to methylenating agent is not limited to any particular value but it is preferred to use 2–20 moles, more preferably 5–10 moles, of N-phenyl carbamates per mole of the methylenating agent. If at least 2 moles of N-phenyl carbamates are used, the formation of by-product tri- or more nuclear polymethylenepolyphenyl carbamates is suppressed, which contributes to a higher yield of the desired 4,4'-diphenylmethane dicarbamates. If the use of N-phenyl carbamates does not exceed 20 moles, the amount of residual N-phenyl carbamates in the reaction solution is sufficiently low to avoid an economic disadvantage that results from the increase in the cost of recovering such residual N-phenyl carbamates.

The amount in which the catalyst is to be used is not limited to any particular value but it is preferred to use 0.1-10 moles, more preferably 0.3-5 moles, of the catalyst per mole of N-phenyl carbamates. If less than 0.1 mole of the catalyst is used, the intended reaction will not be completed and large amounts of unreacted N-phenyl carbamates and intermediate compounds having a methyleneamino bond will remain in the reaction solution. If more than 10 moles of the catalyst is used, the reaction rate is difficult to control and 2,4'-diphenylmethane dicarbamates and polymethylenepolyphenyl carbamates will form as by-products in large quantities.

If the solvent is to be used, its amount also is not limited to any particular value. Preferably, it is used in an amount of 0.1-5 parts by weight, more preferably 0.5-2 parts by weight, per part by weight of N-phenyl carbamates The reaction involved in the method of the present invention is carried out at temperatures not higher than 200° C., preferably in the range of 50-150° C., more preferably in the range of 80-120° C. If the reaction temperature is too low, the intended reaction will not be completed and large amounts of unreacted N-phenyl carbamates and intermediate compounds having a methyleneamino bond will remain in the reaction solution. If the reaction temperature is too high, 2,4'-diphenylmethane dicarbamates and polymethylenepolyphenyl carbamates will form as by-products in large quantities.

The method of the present invention is typically performed either at atmospheric or a superatmospheric pressure, but if necessary, it may be performed in vacuo.

The reaction time varies with other factors including the reaction temperature, the type and amount of catalyst, the presence or absence of solvent, its type and amount, the composition of the feed and the mode of reaction, but typically the range of 0.5-10 h will suffice.

The mode of reaction is not limited in any particular way and it may be carried out by either a batch or continuous method, preferably with stirring. Other methods of reaction that can be used include: 1) performing the reaction with the catalyst being suspended in the reaction mixture or in the form a slurry; 2) performing reaction in a two-liquid phase consisting of an aqueous solution having the catalyst dissolved therein and a solution of N-phenyl carbamates in an organic solvent; and 3) performing the reaction using a fixed catalyst bed.

EXAMPLES

The following examples are provided for the purpose of further illustrating the present invention but are in no way to be taken as limiting. In these examples, the conversion of N-phenyl carbamates, as well as the selectivity therefor, and the yield of 4,4'-diphenylmethane dicarbamates were calculated by the following formulas: Conversion of N-phenyl carbamates Conversion of N-phenyl carbamates =

$$\frac{\text{N-phenyl carbamates consumed (mol)}}{\text{formaldehyde charged (mol)} \times 2} \times 100\,(\%);$$

Selectivity for 4,4'-diphenylmethane dicarbamates =

$$\frac{\text{4,4'-diphenylmethane dicarbamates produced (mol)}}{\text{N-phenyl carbamates consumed (mol)/2} \times 100\,(\%)} \times 100\,(\%):$$

Yield of 4,4'-diphenylmethane dicarbamates =

$$\frac{\text{4,4'-diphenylmethane dicarbamates produced (mol)}}{\text{formaldehyde charged (mol)}} \times 100\,(\%)$$

EXAMPLE 1

A 200- ml glass reactor equipped with a stirrer and a condenser was charged with 56.1 g of nitrobenzene, 55.9 g (0.37 mol) of methyl N-phenylcarbamate, 3.0 g (0.04 mol) of 37% formalin and 38.7 g (0.28 mol) of zinc chloride (anhydride), all of these being added at one time. Reaction was carried out at atmospheric pressure, at 100° C. for 5 h, during which period zinc chloride was suspended in the reaction mixture in the form of a slurry. After completion of the reaction, a sample was taken from the reaction solution and analyzed by high-performance liquid chromatography. The results were excellent: the conversion of methyl N-phenylcarbamate was 101%; the selectivity for dimethyl 4,4'-diphenylmethanedicarbamate was 80%; and the yield of this product was 81%. On the other hand, the selectivity for dimethyl 2,4'-diphenylmethanedicarbamate was 3.9%, and its yield was 4.0%. Thus, the formation of by-product dimethyl 2,4'-diphenylmethanedicarbamate was very small. Bis(N-carbomethoxyaniliano)methane and methyl (N-carbomethoxyanilinomethyl)phenylcarbamate, which were intermediates having a methyleneamino bond, were undetectable. Further, the selectivity for tri- and more nuclear polymethylenepolyphenyl carbamates was very low (1.4%).

Thus, according to the present invention, dimethyl 4,4'-diphenylmethanedicarbamate could be produced with high selectivity and in high yield by a simple procedure of a one-stage condensation reaction between methyl N-phenyulcarbamate and a methylenating agent. Another advantage of the present invention is that the formation of by-product dimethyl 2,4'-diphenylmethanedicarbamate could be substantially suppressed.

EXAMPLE 2

A 200-ml glass reactor equipped with a stirrer and a condenser was charged with 27.95 g of nitromethane, 27.95 g (0.19 mol) of methyl N-phenylcarbamate, 1.5 g (0.02 mol) of 37% formalin and 19.36 g (0.14 mol) of zinc chloride (anhydride), all of these being added at a time. Reaction was carried out at an atmospheric pressure and at 100° C. for 5 h. After completion of the reaction, a sample was taken from the reaction solution and analyzed by high-performance liquid chromatography. The results were excellent: the conversion of methyl N-phenylcarbamate was 100%; the selectivity for dimethyl 4,4'-diphenylmethanedicarbamate was 75%; and the yield of this product was 75%. On the other hand, the selectivity for dimethyl 2,4'-diphenylmethanedicarbamate was 2.4% and its yield was 2.4%. Thus, the formation of dimethyl 2,4'-diphenylmethanedicarbamate was very small. Bis(N-carbomethoxyanilino)methane and methyl (N-carbomethoxyanilinomethyl)phenylcarbamate which were intermediates having a methyleneamino bond were undetectable. Further, the selectivity for tri- and more nuclear polymethylenepolyphenylene carbamates was very low (1.2%).

EXAMPLE 3

A 200-ml glass reactor equipped with a stirrer and a condenser was charged with 27.95 g of nitrobenzene, 27.95 g (0.19 mol) of methyl N-phenylcarbamate, 1.54 g (0.02 mol) of 37% formalin and 31.53 g (0.14 mol) of zinc bromide (anhydride), all of these being added at one time. Reaction was carried out at an atmospheric pressure and at 100° C. for 5 h. After completion of the reaction, a sample was taken from the reaction solution and analyzed by high-performance liquid chromatography. The results were excellent: the conversion of methyl N-phenylcarbamate was 91%; the selectivity for dimethyl 4,4'-diphenylmethanedicarbamate was 86%; and the yield of this product was 78%. On the other hand, the selectivity for dimethyl 2,4'-diphenylmethanedicarbamate was 2.2% and its yield was 2.0%. Thus, the formation of dimethyl 2,4'-diphenylmethanedicarbamate was very small. Bis(N-carbomethoxyanilino)methane and methyl (N-carbomethoxyanilinomethyl)phenylcarbamate which were intermediates having a methyleneamino bond were undetectable. Further, the selectivity for tri- and more nuclear polymethylenepolyphenyl carbamates was very low (0.2%).

EXAMPLE 4

A condensation reaction was performed under entirely the same conditions as in Example 2 except that the solvent nitromethane was replaced by the same part by weight of chlorobenzene. After completion of the reaction, a sample was taken from the reaction solution and analyzed by high-performance liquid chromatography. The results are shown in Table 1.

EXAMPLE 5

A condensation reaction was performed under entirely the same conditions as in Example 2 except that the methyl N-phenylcarbamate was replaced by ethyl N-phenylcarbamate in the same number of moles. After completion of the reaction, a sample was taken from the reaction solution and analyzed by high-performance liquid chromatography. The results are shown in Table 1.

TABLE 1

|  | E4 | E5 |
|---|---|---|
| Conversion of N-phenylcarbamate (%) | 104 | 74 |
| Selectivity |  |  |
| 4,4'-diphenylmethanedicarbamate | 71 | 96 |
| 2,4'-diphenylmethanedicarbamate | 3.1 | 4.6 |
| intermediate* | 0.0 | 0.0 |
| polynuclear compound** | 0.4 | 3.5 |
| Yield |  |  |
| 4,4'-diphenylmethanedicarbamate | 74 | 71 |
| 2,4'-diphenylmethanedicarbamate | 3.2 | 3.4 |

*Example 4: bis(N-carbomethoxyanilino)methane and methyl(N-carbomethoxyanilinomethyl)phenylcarbamate which are intermediates having a methyleneamino bond
Example 5: bis(N-carboethoxyanilino)methane and ethyl(N-carboethoxyanilinomethyl)phenylcarbamate which are intermediates having a methyleneamino bond
**tri- and more nuclear polymethylenepolyphenyl carbamates A zinc halide as a catalyst enables binuclear 4,4'-diphenylmethane dicarbamates to serve as precursors of 4,4'-diphenylmethane diisocyanate 4,4'-MDI, or commonly referred to as "pure MDI") to be produced with high selectivity and in high yield by the one-stage condensation reaction between N-phenyl carbamates and a methylenating agent.

What is claimed is:

1. A method of preparing a 4,4'-diphenylmethane dicarbamate, which comprises condensing a methylenating agent with 2 to 20 moles of an N-phenylcarbamate per mole of the methylenating agent in the presence of a zinc halide.

2. A method according to claim 1 which uses an organic solvent.

3. A method according to claim 1 or 2 wherein said zinc halide is used in an amount of 0.1-10 moles per mole of the N-phenylcarbamate.

4. A method according to claim 1 wherein said zinc halide is zinc chloride ($ZnCl_2$), zinc bromide ($ZnBr_2$) or a mixture thereof.

5. A method of preparing 4,4'-diphenylmethane dicarbamates, which comprises condensing an N-phenyl carbamate with a methylenating agent int he presence of a zinc halide.

6. A method according to claim 1 wherein the N-phenyl carbamate is represented by the following general formula:

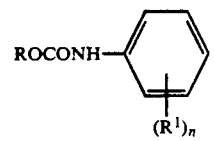

where R is a $C_1$–$C_4$ substituted or unsubstituted alkyl, a $C_5$–$C_9$ cycloalkyl or aralkyl, a phenyl group having at least a $C_1$–$C_4$ straight-chain or branched alkyl group on the benzene ring thereof; R' is a hydrogen atom, a $C_1$–$C_4$ alkyl group, a halogen atom, a nitro group, a cyano group, a $C_1$–$C_4$ alkoxy group, and an aralkyl or phenyl group having at least a $C_1$–$C_4$ straight-chain or branched alkyl group on the benzene ring thereof, provided that R' is bonded to the urethane group in the ortho- or meta-position; and n is an integer of 0–4, provided that when $n \geq 2$, R' may be the same or different.

7. A method according to claim 6 wherein the N-phenyl carbamate represented by the general formula is selected from methyl N-phenylcarbamate, ethyl N-phenylcarbamate, n-propyl N-phenylcarbamate, isopropyl N-phenylcarbamate, n-butyl N-phenylcarbamate, isobutyl N-phenylcarbamate, tert-butyl N-phenylcarbamate, pentyl N-phenylcarbamate, hexyl N-phenylcarbamate, cyclohexyl N-phenylcarbamate, methyl N-o- or m-tolylcarbamate, ethyl N-o- or m-tolylcarbamate, propyl N-o- or m-tolyl carbamate, or isomers thereof, butyl N-o- or m-tolylcarbamate, or isomers thereof, methyl N-o- or m-chlorophenylcarbamate, ethyl N-o- or m-chlorophenylcarbamate, propyl N-o- or m-chlorophenylcarbamate, or isomers thereof, butyl N-o- or m-chlorophenylcarbamate, or isomers thereof, methyl N-2,6-dimethylphenylcarbamate, ethyl N-2,6-dimethylphenylcarbamate, propyl N-2,6-dimethylphenylcarbamate, or isomers thereof, or butyl N-2,6-dimethylphenylcarbamate, or isomers thereof.

8. A method according to claim 1 wherein the methylating agent is selected from the group consisting of formalin paraformaldehyde, trioxane, tetraoxane, a lower alkoxymethane, a diacycloxymethane having a lower carboxy group and a mixture thereof.

* * * * *